United States Patent [19]

Watson et al.

[11] Patent Number: 4,809,706
[45] Date of Patent: Mar. 7, 1989

[54] INCENTIVE INHALATION SPIROMETER APPARATUS

[76] Inventors: Robert L. Watson, 201 W. Laurel St., Unit 312, Tampa, Fla. 33602; Robert L. Rayburn, P.O. Box 11, North Salt Lake, Utah 84054

[21] Appl. No.: 143,191

[22] Filed: Jan. 13, 1988

[51] Int. Cl.[4] .............................................. A61B 5/06
[52] U.S. Cl. ..................................... 128/725; 128/914
[58] Field of Search .................. 272/99; 128/716, 719, 128/725, 720, 911, 914, 200.21

[56] References Cited

U.S. PATENT DOCUMENTS

| 3,635,214 | 1/1972 | Rand et al. | 128/2 |
|---|---|---|---|
| 4,025,070 | 5/1977 | McGill et al. | 272/99 |
| 4,096,855 | 6/1978 | Fleury, Jr. | 128/2 |
| 4,188,946 | 2/1980 | Watson et al. | 128/204 |
| 4,210,155 | 7/1980 | Grimes | 128/727 |
| 4,221,130 | 9/1980 | Burrows | 128/719 |
| 4,259,951 | 4/1981 | Chernack et al. | 128/725 |
| 4,269,196 | 5/1981 | Toms et al. | 128/727 |
| 4,275,722 | 6/1981 | Sorensen | 128/203.12 |
| 4,299,355 | 11/1981 | Hakkinen | 128/200.21 |
| 4,301,810 | 11/1981 | Belman | 272/99 |
| 4,320,754 | 3/1982 | Watson et al. | 128/204 |
| 4,327,740 | 5/1982 | Shuman | 272/99 |
| 4,336,798 | 6/1982 | Beran | 128/911 |
| 4,391,283 | 7/1983 | Sharpless et al. | 128/725 |
| 4,425,923 | 1/1984 | Gordon et al. | 28/727 |
| 4,462,397 | 7/1984 | Suzuki | 128/911 |
| 4,509,688 | 4/1985 | Gagne et al. | 128/200.21 |
| 4,669,461 | 6/1987 | Battaglia et al. | 128/202 |

OTHER PUBLICATIONS

"The DHD Coach", DHD Medical Products, Canastota, NY (undated).

Primary Examiner—Edward M. Coven
Assistant Examiner—John P. Lacyk
Attorney, Agent, or Firm—Walter C. Farley

[57] ABSTRACT

An incentive lung exercise apparatus includes an inhalation spirometer, a coupling attached thereto with a unidirectional outlet valve and a source of oxygen. A relatively long flexible hose connects this portion of the structure to a mouthpiece or face mask and medication nebulizer which can be held by a patient. Oxygen and medication can be administered while the patient is using the spirometer structure for lung exercise following surgery or the like. Oxygen is passed through a small hose within the major hose, leaving a substantial volume to retain exhaled gas which is then rebreathed, giving the patient greater incentive to utilize the apparatus for maximum lung inflation. A further small hose can be included and connected to an infrared capnograph for monitoring $CO_2$ in the hose. Control of the depth of respiration is accomplished by varying the oxygen flow and inspired carbon dioxide content as judged by the analyzed expired endtidal carbon dioxide content.

6 Claims, 3 Drawing Sheets

INCENTIVE INHALATION SPIROMETER APPARATUS

This invention relates to an inhalation system for exercising the lungs of an individual and, in particular, to an apparatus which induces the individual to undertake and maintain an exercise regimen.

BACKGROUND OF THE INVENTION

The desirability of exercising a patient's lungs, particularly a postoperative patient, has long been recognized. It is essential for the patient to expand the lungs as soon as possible after surgery, and in some other medical situations, so that all of the alveoli of the lungs are inflated.

For this purpose, many devices known as spirometers have been devised. Although these spirometers take various forms, those which are particularly valuable in connection with post-surgical patients involve a housing with an inlet and an outlet and some form of valving arrangement so that air can be inhaled by the patient from the outlet, the path between the inlet and outlet being constricted in some fashion so that a measured amount of flow resistance is provided. This forces the patient to work against the resistance. Many such devices have indicators which can be observed by the patient as he or she inhales. One such device which is particularly beneficial is known as "the DHD coach" and is sold by DHD Medical Products Company and is identified as Model 22-4000. This particular device has a plastic housing with two major portions, one portion being a hollow cylinder with a piston movable therein. The piston is surrounded by gaskets means so that it is slidable in the cylinder and has a valve to permit a small amount of flow through the piston. The other portion has a tapered vertical channel, the bottom of which is narrower than the top. A valve member, referred to as the "coach" is freely movable in the channel and moves to the bottom, narrow end under the force of gravity. Channels within the housing are constructed so that inhalation by the patient through an attached hose draws the "coach" upwardly into the wider portion of the channel, allowing air to flow and draw the piston upwardly. In order to maintain the coach at an elevated position, the air flow rate must be increased because of the increasing width of the channel. Thus, the height of the "coach" indicates inhalation flow rate while the level of the piston indicates the total volume inhaled.

As indicated above, such devices are particularly helpful, but the problem of inducing the patient, who is frequently groggy from anesthetic and may be uncomfortable from the surgery itself, to actually use the device effectively without continual supervision is a difficult one. It is often necessary for medical personnel to visit the patient for initial instruction on how to use the spirometer, then return to be sure that it has been used, and then return again to supply nebulized medication for inhalation, commonly in the form of a decongestant or bronchial dilator. It may also be necessary to supply the patients with breathing oxygen. These various forms of attention add to the cost of postoperative care, unduly tire the patient and occupy medical personnel who are commonly needed elsewhere.

SUMMARY OF THE INVENTION

Accordingly, an object of the present invention is to provide an incentive spirometer which induces the patient to use the spirometer more effectively by allowing for a measured inhalation of exhaled carbon dioxide.

A further object is to provide an apparatus which can be employed to supply the patient with oxygen, medication or both while the spirometer is being employed without the necessity to remove the breathing tube from the mouth or face mask after each inhalation.

A still further object of the invention is to provide such an apparatus which is convenient and simple to use.

Briefly described, the invention includes a lung exercise apparatus comprising the combination of spirometer means for providing a measured amount of flow resistance to air drawn therethrough in one direction and for substantially preventing air flow therethrough in the opposite direction, the spirometer means having an air inlet and an outlet. Means defining an elongated, flexible first hose is connected at one end to the spirometer outlet and to a mouthpiece at the other end for forming a passage through which the patient can inhale through the spirometer means. A nebulizer having an inlet and an outlet is attached to the passage adjacent the mouthpiece. An elongated, flexible second hose is provided within the first hose, the second hose having a diameter somewhat smaller than the first hose. One end of the second hose is attached near the spirometer outlet through a wall of the first hose to a source of oxygen, the other end of the second hose being connected to aspirate medication from the nebulizer. A unidirectional valve is connected in the passage for allowing gas to flow only out of the first hose. The valve is preferably somewhat closer to the spirometer than to the mouthpiece so that the length of the hose forms a substantial volume for containing gas exhaled by the patient for rebreathing.

BRIEF DESCRIPTION OF THE DRAWINGS

In order to impart full understanding of the manner in which these and other objects are attained in accordance with the invention, particularly advantageous embodiments thereof will be described with reference to the accompanying drawings, which form a part of this specification and wherein.

DESCRIPTION OF THE PREFERRED EMBODIMENTS

Figure 1:
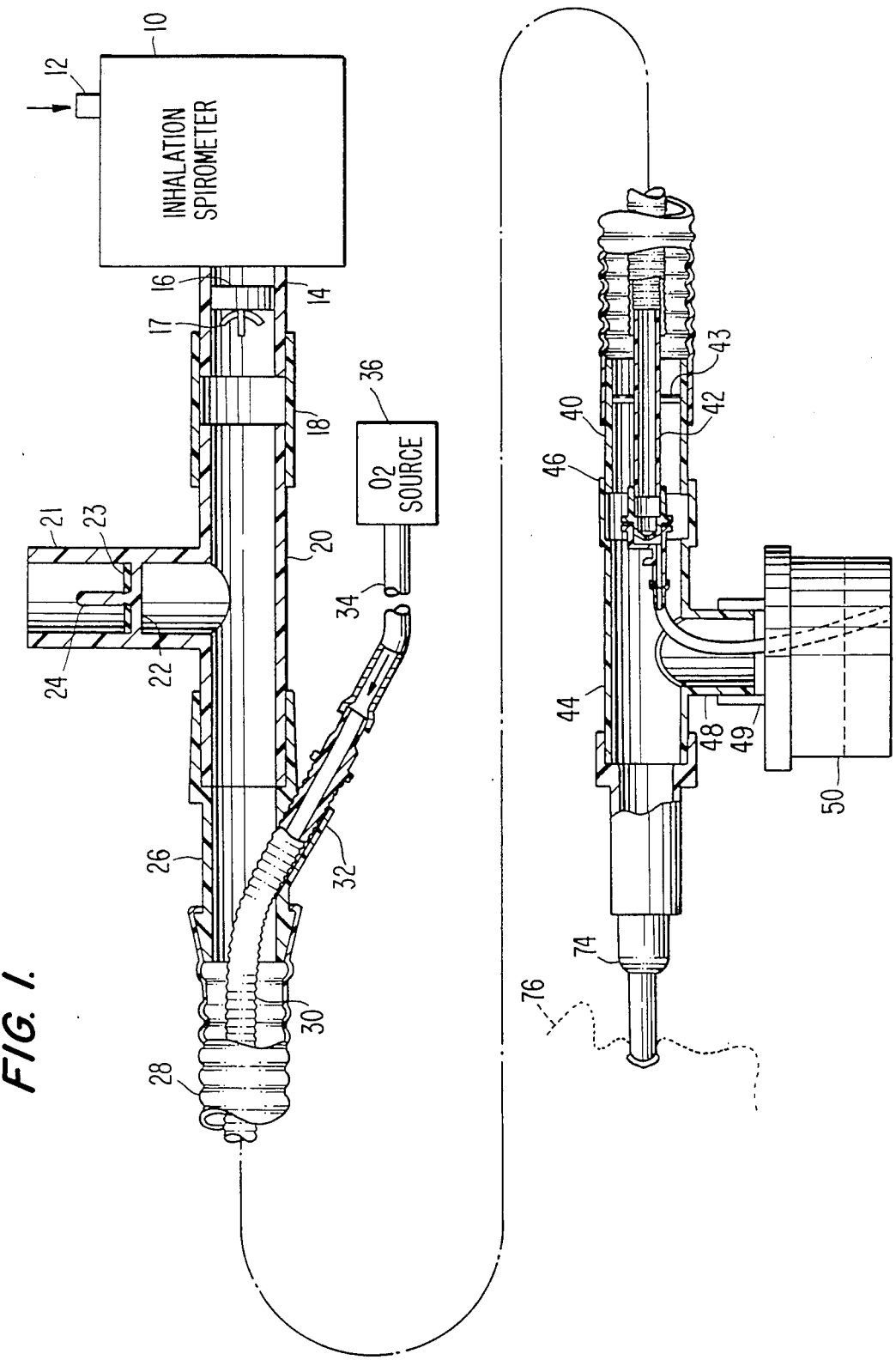
FIG. 1 is a foreshortened side elevation, in longitudinal cross-section, of one embodiment of an apparatus in accordance with the invention.

The apparatus includes spirometer means comprising an inhalation spirometer 10 having an air inlet 12 and an outlet 14. Spirometer 10 can be any of a variety of commonly available devices, as discussed above, which provide an air flow path which presents a predetermined amount of flow resistance to the air passing therethrough. Preferably, the air path includes a valve device such as unidirectional valve 16. Valve 16 is a conventional type of flap valve having a web with openings therethrough and a flexible disk 17 which can be moved to the position shown by air flowing out of the spirometer to permit free flow thereof, but which closes the openings when air attempts to flow in the opposite direction.

Outlet 14 from the spirometer is coupled, as by a tube 18, to a T-shaped coupling 20 having a conduit portion 21 which also contains a unidirectional valve. This unidirectional valve includes a web or spider 22 having openings therethrough and a disk 23 of flexible material held on a central post 24. Flap 23 is sufficiently flexible to move aside when air attempts to flow out through conduit portion 21 but closes the openings in web 22 to prevent the inflow of air.

Coupling 20 is connected to a further coupling 26 the other end of which is connected to an elongated first flexible hose 28 which, together with the coupling members, defines a passage for the flow of air to the patient. Within hose 28 is a smaller diameter second hose 30 which forms a flow path for oxygen. One end of flow path 30 terminates in coupling 26 at a lateral outlet 32 which can be connected by a conventional hose 34 to a source of oxygen 36. The coupling member 26 with the lateral connection is, in itself, a conventional coupling part.

Hoses 28 and 30 are both of a rather conventional type of extruded or molded corrugated plastic material. It is significant that hose 30 is considerably smaller than hose 28, leaving a substantial volume within hose 28 for the flow of air as well as for the storage of a quantity of exhaled air. Typically, hose 28 has an inner diameter in the order of 0.75 in or greater while hose 30 has an outer diameter in the order of 0.25 in. Hose 28 is preferably on the order of 3 feet in length.

Figure 2:
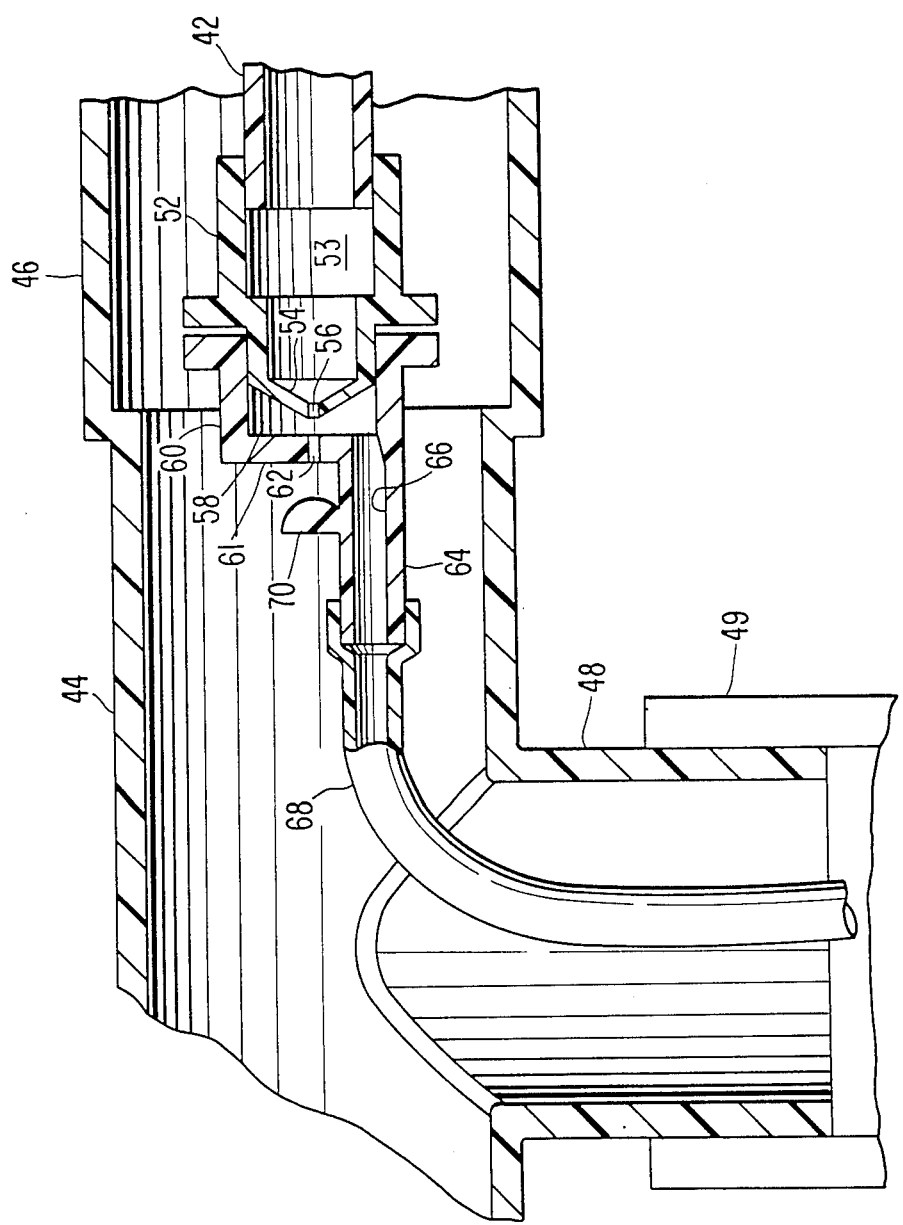
FIG. 2 is an enlarged side elevation of a medication dispenser and nebulizer usable in the apparatus of FIG. 1.

Attached to the other end of hose 28 is a coupling member 40 which includes a straight cylindrical section having a coaxial interior tube 42 one end of which is attached to the end of hose 30 while the other end is connected to a nebulizer apparatus best seen in FIG. 2. Coupling member 40 also includes a spider 43 which positions tube 42 in member 40. A T-shaped coupling 44 has an enlarged end portion 46 which surrounds the other end of member 40 and a laterally extending tube portion 48 which is attached to a tubular coupling portion 49 at the top of a medication container 50.

The end of tube 42 is attached to a cylindrical tubular member 52 the interior of which forms a first chamber 53 and which has, at its downstream end, a conical portion 54 the point of which is penetrated by a first gas outlet opening in the form of a small hole 56, best seen in FIG. 2, which has a diameter on the order of 0.05 inches but which, more significantly, is substantially smaller than the passageway within hose 30 and interior tube 42.

The protruding end of member 52 which terminates in conical portion 54 is received within a generally cylindrical second chamber 58 within a cylindrical body 60 which has an end wall 61 penetrated by a hole comprising a second outlet opening 62 which is coaxial with and substantially the same diameter as hole 56. Body 60 is also provided with a somewhat smaller tubular extension 64 which protrudes in an axial direction from the lower portion of body 60 and which has an interior passageway 66. Passageway 66 communicates with the chamber 58 and with the interior of a relatively small, flexible inlet hose or tube 68 which is firmly attached to the end of extension 64 and which extends outwardly through tubular portion 48 into the medication receptacle 50. On the upper side of extension 64 is an upward protrusion 70 having a hemispherical surface facing toward opening 62, the hemispherical surface being substantially coaxially aligned with openings 62 and 56.

The other end of coupling member 44 is connected to a mouthpiece 74 having an opening shaped to be comfortably received within the mouth of the user indicated generally at 76. Preferably, mouthpiece 74 has a generally fan-shaped mouth piece portion. Coupling member 44 can also be attached to a standard face mask.

In use, the mouthpiece is placed in the patients mouth and the patient is instructed to breathe in and out without removing the mouthpiece from his or her mouth and without nasal breathing. The patient is also instructed to breathe slowly and deeply, filling the lungs to the maximum extent possible on each breath. When the patient inhales, flexible member 17 of valve 16 allows air to pass through the spirometer, through hose 28 and the various couplings, and through the mouthpiece 74 into the patients lungs. When the patient exhales, air passes through hose 28, closing valve 16 but opening valve flap 23, allowing the air to pass out through conduit portion 21.

It is particularly important to recognize, however, that a significant quantity of exhaled gas, containing carbon dioxide, will remain within hose 28. With the dimensions suggested above, the length of hose contains approximately 14 cubic inches of exhaled air.

When the patient breaths in again, this exhaled air returns to the lungs along with some fresh air drawn in through the spirometer and small amount of oxygen if it is being used. The presence of the rebreathed $CO_2$ in the lungs from the tube 28 causes the patient to have the feeling that he or she must breathe again. This is similar to the feeling which one experiences after holding one's breath for a period of time and allowing the carbon dioxide to build up in the lungs. The existence of this rebreathed air and carbon dioxide causes the next breath to be a deeper one, thus creating a greater incentive for the patient to not only continue breathing but to breathe deeply. This has the beneficial effect of giving the patient the incentive to expand the alveoli of his or her lungs to the maximum. The amount of rebreathed $CO_2$ is controlled by the oxygen flow through tube 30 into tube 28. The amount of $CO_2$ rebreathed is decreased by increasing the oxygen flow. Thus, the depth of breathing can also be controlled.

If circumstances are such that the patient is to also be supplied with oxygen, the source 36 can be valved open to permit the desired oxygen flow. In addition, medication can be inserted into medication container 50 so that the flow of oxygen provides medication, particularly at the beginning of the exercise therapy.

As oxygen passes through tube 30 and interior tube 42 into the interior of cylindrical member 52, positive pressure is produced therein and a small stream of oxygen passes at high velocity through coaxial openings 56 and 62, creating a negative pressure in chamber 58. This negative pressure draws medication through hose 68, the lower end of which is immersed in medication carried in container 50, and through passage 66 into chamber 58. The medication thus aspirated is carried by the stream of oxygen passing through openings 56 and 62 so that droplets of the medication are propelled out of opening 62 and against the hemispherical surface of protrusion 70 where the droplets are caused to break up into very small, vapor-like droplets. This produces a fog of medication within coupling 44 which is then drawn into the patient's lungs with the next inhalation. The medication used can be any of a number of conventional medications such as bronchial dilators, decongestants and the like depending upon the medical indications.

It will be recognized that the arrangement of components is such that the spirometer, the oxygen coupling and the outlet valve are positioned together so that they can be placed on a table near the patient and need not be held. With the length of hose of approximately 3 ft., the patient can hold the nebulizer and coupling, which is very small and light, and need not be concerned about manipulating any other hardware. He or she can then breathe in and out freely, as described above, gaining incentive to do so by a quantity of rebreathed carbon dioxide. The addition of oxygen flow does not diminish the incentive factor of the carbon dioxide since it is still rebreathed, although with a higher proportion of oxygen and lower proportion of other gases than would be found in the air alone.

Figure 3:
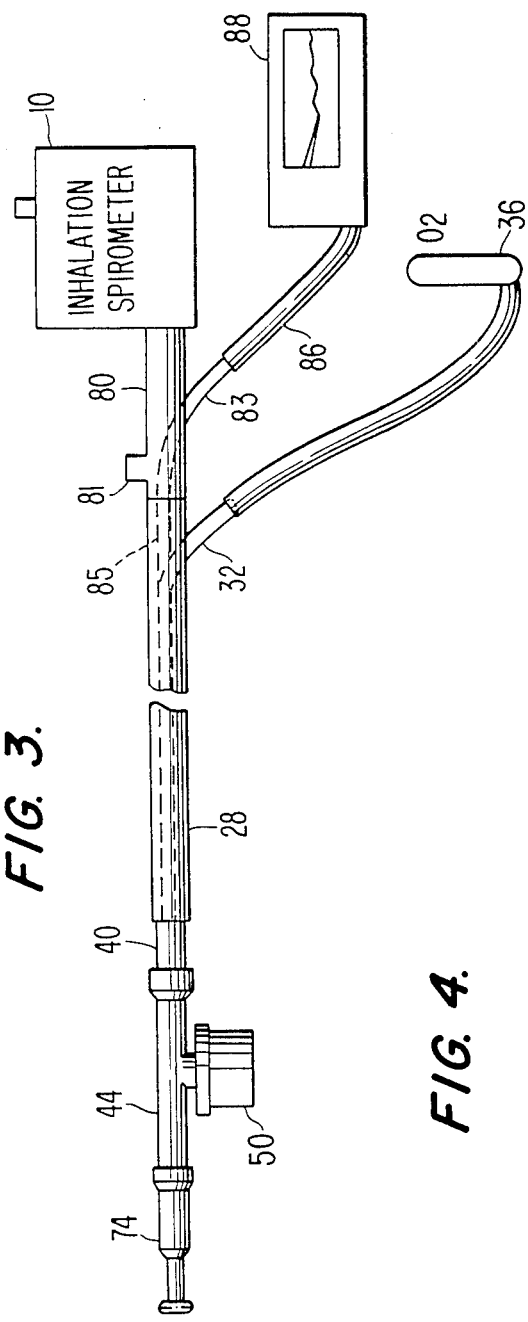
FIG. 3 is a schematic representation of a further embodiment of an apparatus in accordance with the invention.
Figure 4:
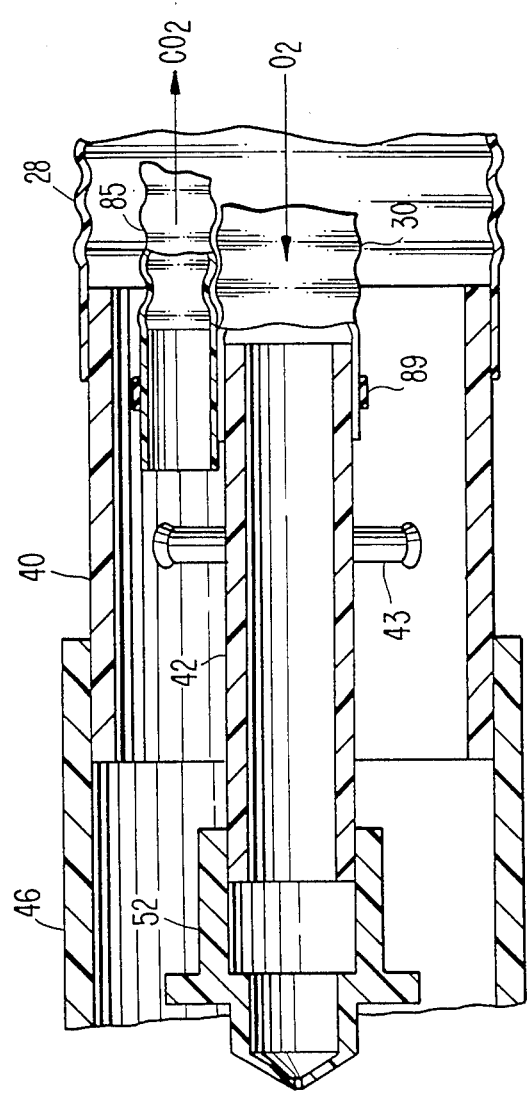
FIG. 4 is an enlarged side elevation of the portion of the apparatus of FIG. 3 adjacent the nebulizer.

A further embodiment of an apparatus in accordance with the invention is illustrated in FIGS. 3 and 4 in which it will be noted that many of the components employed are the same as those used in connection with FIGS. 1 and 2 and are identified by the same reference numerals.

However, in FIG. 4, the coupling member 20 is replaced by a coupling member schematically illustrated at 80 having a lateral, unidirectional valve 81 which functions in a manner identical to the valve within tubular extension 21 and also has an outwardly extending gas coupling 83 which is structurally substantially identical to coupling 32. Coupling 83 is connected to an interior third hose 85 the interior of which is isolated from the interior of hose 28 and also the interior of hose 30. Coupling 83 is connected by a hose 86 to a device for recording carbon dioxide which is conventionally known as an infrared capnograph 88.

As best seen in FIG. 4, hose 85 extends side-by-side along the interior of hose 28 with hose 30 and terminates within coupling member 40 adjacent tube 42. The open end of hose 85 can be held in that position by any convenient means such as an elastic band or the like 89.

The infrared capnograph functions by extracting a quantity of gas through tubes 85 and 86 and coupling 83 and measuring and recording the carbon dioxide content of that gas. The open distal end of tube 85 is positioned in the vicinity of the mouthpiece, but away from the oxygen inlet, to obtain a representative sample of the carbon dioxide in the air exhaled by the patient.

A person can maintain an average arterial carbon dioxide level equivalent to approximately 40 mm of mercury when fresh gas flow in the coaxial circuit is equal to 4000 cc per square meter of body surface area. When fresh gas oxygen flow is reduced, the amount of carbon dioxide rebreathing is increased and causes a stimulus to breathe by the increased effect of the arterial carbon dioxide on the carotid artery carbon dioxide chemoreceptors. The provision of the infrared capnograph allows monitoring of the level of carbondioxide with the same apparatus being used for inhalation therapy and without any separate steps. This measurement can be employed to evaluate the success of the therapy and also, if necessary, to adjust the level of oxygen flow to the patient.

While certain advantageous embodiments have been chosen to illustrate the invention, it will be understood by those skilled in the art that various changes and modifications can be made therein without departing from the scope of the invention as defined in the appended claims.

What is claimed is:

1. Lung exercise apparatus comprising the combination of spirometer means for providing a measured amount of flow resistance to air drawn therethrough in one direction and for substantially preventing air flow therethrough in the opposite direction, said spirometer means having an air inlet and an outlet;

means defining an elongated, flexible first hose connected at one end to said outlet and having patient-engageable means at the other end for forming a passage through which a patient can inhale through said spirometer means;

nebulizer means having a gas inlet, a source of medication, and a medication outlet;

means for attaching said medication outlet adjacent said patient-engageable means;

an elongated, flexible second hose within said first hose, said second hose having a diameter significantly smaller than said first hose, said second hose having a first end near said spirometer outlet and a second end near said patient-engageable means;

means at said first end of said second hose for connecting said second hose through a wall of said first hose to a source of oxygen;

means at said second end of said second hose for connecting said second hose to said gas inlet of said nebulizer; and unidirectional valve means in said first hose for allowing gas to flow out of said hose, said valve means being separated from said patient-engageable means by a distance greater than the separation between said valve means and said spirometer outlet to form a substantial volume within said first hose for containing gas exhaled by said patient for rebreathing.

2. An apparatus according to claim 1, wherein said unidirectional valve means is positioned adjacent said spirometer outlet.

3. An apparatus according to claim 1, wherein said source of medication comprises a container coupled to said first hose near said patient-engageable means, said nebulizer means further comprising a first chamber coupled to receive oxygen from said second hose through said gas inlet, said first chamber having a first gas outlet opening significantly smaller than said gas inlet;

means defining a second chamber adjacent said first chamber, said first gas outlet opening comprising a gas inlet to said second chamber, said second chamber further having an inlet tube communicating with said source of medication, and a second outlet opening comprising said medication outlet and coaxially aligned with said gas outlet opening whereby flow of oxygen through said coaxially aligned openings aspirates medication from said source of medication into said second chamber and out of said outlet opening.

4. An apparatus according to claim 3, wherein said nebulizer means further comprises means defining a hemispherical surface aligned with said medication outlet opening for breaking medication emerging from said medication outlet opening into small droplets to thereby form a fog of medication in said first hose.

5. An apparatus according to claim 4 and further comprising an elongated, flexible third hose within said first hose, said third hose having a diameter significantly smaller than said first hose, said third hose having a first end near said spirometer outlet and a second end near said patient engageable means;
- means at said first end of said third hose for connecting said third hose through a wall of said first hose; and
- means outside of said first hose connected to said third hose for sampling and recording levels of carbon dioxide from within said first hose.

6. An apparatus according to claim 1 and further comprising an elongated, flexible third hose within said first hose, said third hose having a diameter significantly smaller than said first hose, said third hose having a first end near said spirometer outlet and a second end near said patient-engageable means;
- means at said first end of said third hose for connecting said third hose through a wall of said first hose; and
- means outside of said first hose connected to said third hose for sampling and recording levels of carbon dioxide from within said first hose.

* * * * *